United States Patent [19]

Yamamoto et al.

[11] 4,196,155
[45] Apr. 1, 1980

[54] PROCESS FOR PREPARING ORGANIC PHOSPHORUS COMPOUNDS

[75] Inventors: Isamu Yamamoto, Zushi; Eiichi Noda; Yoshiaki Noguchi, both of Yokohama, all of Japan

[73] Assignee: Mitsui Toatsu Chemicals, Incorporated, Tokyo, Japan

[21] Appl. No.: 919,489

[22] Filed: Jun. 27, 1978

[30] Foreign Application Priority Data

Jul. 22, 1977 [JP]  Japan .................................. 52-87453

[51] Int. Cl.$^2$ ............................................... C07F 9/40
[52] U.S. Cl. .................................. 260/931; 106/15.05; 106/16; 106/18.18; 106/18.19; 260/45.7 P; 260/969; 260/973; 260/977; 260/DIG. 24; 521/85; 521/108
[58] Field of Search ............... 260/973, 931, 977, 969, 260/DIG. 24

[56] References Cited

U.S. PATENT DOCUMENTS

| | | | |
|---|---|---|---|
| 3,391,226 | 7/1968 | Birum et al. | 260/931 |
| 4,044,076 | 8/1977 | Kametani et al. | 260/931 |
| 4,066,730 | 1/1978 | Mimura et al. | 260/931 |

*Primary Examiner*—Mary C. Lee
*Attorney, Agent, or Firm*—Fisher, Christen & Sabol

[57] ABSTRACT

A process for preparing an organic phosphorous compound of the general formula

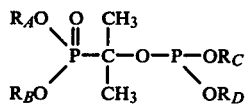

wherein $R_A$ represents

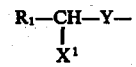

where
$X^1$ is a halogen atom,
Y is —CH$_2$— or —CH$_2$—CH$_2$—, and
$R_1$ is H or CH$_3$ when Y is —CH$_2$—CH$_2$—, or H, CH$_3$ or C$_2$H$_5$ when Y is —CH$_2$—,
$R_B$ represents an alkyl group having from 1 to 4 carbon atoms or a halogenated alkyl group having from 2 to 4 carbon atoms,
$R_C$ represents

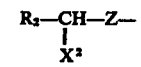

where
$X^2$ is a halogen atom,
Z is —CH$_2$— or —CH$_2$—CH$_2$—, and
$R_2$ is H or CH$_3$ when Z is —CH$_2$—CH$_2$—, or H, CH$_3$ or C$_2$H$_5$ when Z is —CH$_2$—, and
$R_d$ represents an alkyl group having from 1 to 4 carbon atoms or a halogenated alkyl group having from 2 to 4 carbon atoms,
the process including the steps of reacting a cyclic halogenophosphite with a cyclic phosphorous acid and acetone in a molar ratio of 1:1:1, reacting the resulting product with a molecular halogen $X^2_2$ wherein $X^2$ is as defined above to obtain a first product and, esterifying said first product with an alkyl alcohol or halogenated alkyl alcohol or an alkylene oxide or halogenated alkylene oxide to obtain said organic phosphorous compound.

17 Claims, No Drawings

PROCESS FOR PREPARING ORGANIC PHOSPHORUS COMPOUNDS

BACKGROUND OF THE INVENTION

This invention relates to a novel process for preparing organic phosphorus compounds which are useful as a flame retardant of an addition type for polyurethane foam.

The organic phosphorus compounds obtained according to the process of the invention are not only very useful as a flame retardant of an addition type for polyurethane foam, but also effective in flame retardation of synthetic fibers, natural fibers, polyvinyl chloride, polystyrene, polyester, polyethylene, etc., apart from the polyurethane foam.

It is well known that phosphonate polymers serving as flame retardant can be obtained by reacting a cyclic halogenophosphite expressed by a general formula (I) or (II)

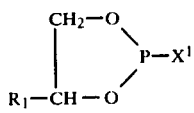

(in which $R_1$ represents a hydrogen atom, a methyl group or an ethyl group, and $X^1$ represents a halogen atom), or

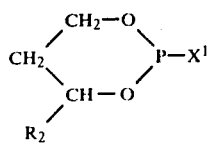

(in which $R_2$ represents a hydrogen atom or a methyl group, and $X^1$ represents a halogen atom) with acetone. However, these phosphonate polymers encounter several problems: (1) The compounds having an end group of P—X (where X represents halogen) are rendered acidic when coexisting with water, so that when these compounds are employed as flame retardant for polyurethane foam, the acidic material produced will serve to inactivate a catalyst for polyurethane, making it difficult to produce a polyurethane foam with stable physical properties; and (2) they are high polymer, so the phosphorus compounds are very viscous and accordingly poor in miscibility with polyether, thus a satisfactory level of flame retardation of the resulting foam being not achievable.

In general, the polyurethane is foamed by the use of water and an alkaline substance. Accordingly, the flame retardant of an addition type for the polyurethane foam should be stable upon mixing with water without suffering from hydrolysis and producing any acidic substance.

One of important physical properties that the flame retardant should possess is low viscosity. In this sense, compounds of such high viscosity as the before-mentioned polymers are not preferable for use as flame retardant. When applied, the flame retardant must be dissolved in polyether as quickly as possible.

There are known a number of flame retardants containing one phosphorus atom in the molecule thereof. Typical of such flame retardants which have been widely applied are tris(chloroethyl)phosphate, tris(2,3-dichloropropyl)phosphate, and tris(2-chloropropyl)phosphate. These retardants are known to be so volatile that a polyurethane foam using such retardants is lowered in non-inflammability during storage since the retardant readily evaporates or volatilizes.

We have made for a long time a study of addition type flame retardants for polyurethane foam which are hard to hydrolyze, which have so low a viscosity as to allow good miscibility with polyether, and which are less volatile during storage of once produced urethane foam. As a result of the study, it has been found that organic phosphorus compounds expressed by the following general formula (VII) are very favorable as flame retardant

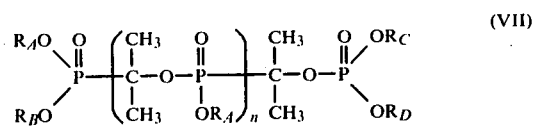

(VII)

(in which $R_A$ and $R_C$ independently represent

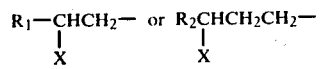

(where X is a halogen atom and $R_1$ is a hydrogen atom, a methyl group or an ethyl group), $R_B$ and $R_D$ independently represent an alkyl group having from 1 to 4 carbon atoms or a halogenated alkyl group having from 2 to 4 carbon atoms and n is an integer from 0 to 3).

We have already proposed a process of preparing such organic phosphorus compounds and also a flame retarder or flameproof composition using the organic phosphorus compounds for addition to polyurethane resin.

According to this production process, the organic phosphorus compounds of the above formula are produced by interacting a cyclic halogenophosphite of the afore-mentioned formula (I) or (II) and acetone, followed by halogenation and esterification. The compounds obtained by the process are very useful not only as an addition-type flame retardant for polyurethane foam, but also as a retardant for synthetic fibers, natural fibers, polyvinyl chloride, polystyrene, polyester, polyethylene, etc. However, the process has a disadvantage that since the polymerization reaction proceeds within a very short period (0-30 minutes) unless the reaction product is immediately subjected to a subsequent halogenation after the interaction of the cyclic halogenophosphite of formula (I) or (II) and acetone, a very severe reaction control is needed.

If the reaction control is insufficient for suppressing the polymerization, polymeric phosphorus compounds corresponding to those of the formula (VII) where n>3 are undesirably formed. These polymers preferentially react with acetone and thus acetone is consumed to produce undesirable by-products. Even if a mole ratio of acetone is decreased, part of the starting cyclic halogenophosphite of formula (I) or (II) will remain unreacted with acetone. The unreacted halogenophosphite will subsequently be halogenated and esterified to secondarily produce phosphoric acid esters having only one phosphorus atom therein. On the contrary, even if a greater amount than that required for the reaction is used to avoid formation of the by-products, the polymerization reaction will proceed unfavorably.

When there is used, as a flame retardant for urethane foam, the organic phosphorus compound obtained by the process which contains polymers corresponding to those of the general formula (VII) wherein n is greater than 3 and phosphoric acid esters having only one phosphorus atom therein, these by-products present the following disadvantages: the polymers are so poor in miscibility with polyether that a urethane foam with stable physical properties can not be obtained, and can not impart satisfactory non-inflammability to the urethane foam; and the phosphoric acid esters containing one phosphorus atom therein do not contribute to the improvement in non-inflammability of the polyurethane foam since they readily evaporate or volatilize during the foaming or blowing operation of polyurethane and during storage of once produced foam over a long time.

The prior process of producing the compounds of the formula (VII) must be conducted under a very severe reaction control. Otherwise, the undesirable polymers as well as the phosphoric acid esters containing one phosphorus atom are invariably produced secondarily, requring an additional equipment for separating such by-products from the compound of the formula (VII). If the organic phosphorus compound containing such by-products are used an addition-type flame retardant for polyurethane foam, these by-products will serve to lower the physical properties and non-inflammability of the produced urethane foam.

SUMMARY OF THE INVENTION

It is an object of the present invention to provide a process for preparing an addition-type flame retardant for polyurethane foam which has so low a viscosity as to allow rapid mixing with polyether, which is hardly hydrolyzed upon mixing with water, and which is hard to evaporate or volatilize during storage of produced urethane foam.

It is another object of the present invention to provide a novel process for preparing an organic phosphorus compound containing two phosphorus atoms in the molecule thereof and expressed by the general formula (VI) appearing hereinafter, which is most suitable as an addition-type flame retardant for polyurethane foam.

It is a further object of the present invention to provide a novel process for preparing an organic phosphorus compound expressed by the general formula (VI) appearing hereinafter, in which side production of polymers corresponding to those of the general formula (VII) where n is greater than 3 and of phosphoric acid esters containing one phosphorus atom is suppressed to a considerable extent.

It is a still further object of the present invention to provide a process for preparing organic phosphorus compounds in which severe control of reaction conditions is not necessary and which is advantageous from a viewpoint of economy.

In accomplishing the foregoing objects, there is provided according to the present invention a process for preparing organic phosphorus compounds, which includes the steps of:

reacting (a) a cyclic halogenophosphite expressed by the above general formula (I) or (II) with (b) a cyclic phosphous acid ester expressed by the general formula (III)

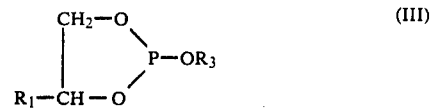

(in which $R_1$ has the same meaning as defined above, and $R_3$ represents an alkyl group having from 1 to 4 carbon atoms or a halogenated alkyl group having from 2 to 4 carbon atoms) or the general formula (IV)

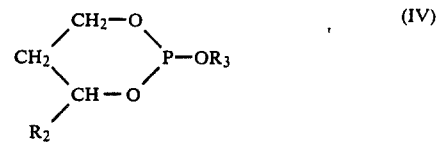

(in which $R_2$ and $R_3$ have the same meanings as defined above), and (c) acetone in a mole ratio of 1:1:1;

subjecting the resulting reaction product to halogenation to give a compound expressed by the general formula (V)

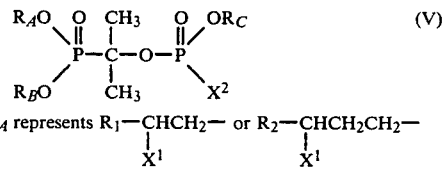

(in which $R_A$ represents 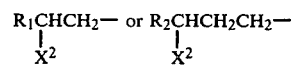 or 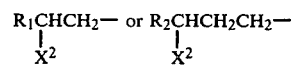

formed by ring cleavage of the compound of the general formula (III) or (IV), $R_B$ represents a group corresponding to $R_3$ of the compound of the general formula (III) or (IV), $R_C$ represents $$R_1CHCH_2- \text{ or } R_2CHCH_2CH_2-$$
$$\underset{X^2}{|} \qquad \underset{X^2}{|}$$

formed by ring cleavage of the compound of the general formula (I) or (II), and $X^1$ of the $R_A$ represents the halogen atom derived from the compound of formula (I) or (II), and $X^2$ of the $R_C$ represents the halogen atom derived from the halogenation reaction); and esterifying the compound of the general formula (V) to give an organic phosphorus compound expressed by the general formula (VI)

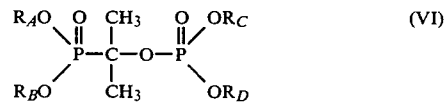

(in which $R_A$, $R_B$ and $R_C$ have the same meanings as defined in formula (V), and $R_D$ represents an alkyl group having from 1 to 4 carbon atoms or a halogenated alkyl group having from 2 to 4 carbon atoms).

DETAILED DESCRIPTION OF THE INVENTION

The compound of the general formula (I) or (II) which is used as starting material in the practice of the invention is obtainable by reacting 1 mole of 1,2-glycol or 1,3-glycol with 1 mole of phosphorus trihalide according to the following reaction formula (1) using 1,2-glycol

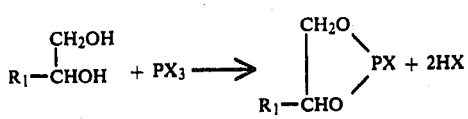

(1)

Similarly, the compound of the general formula (III) or (IV) is obtainable by reacting for esterification the compound of the general formula (I) or (II) with an oxide or an alcohol according to the following reaction formula (2) using the compound of the general formula (I)

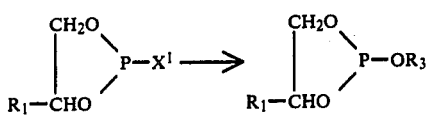

(2)

The process of the present invention will be particularly described using the cyclic halogenophosphite expressed by the general formula (I) and the cyclic phosphorous acid ester expressed by the general formula (III) as starting materials. Needless to say, the process using combinations of compounds of the formulae (II) and (III), compounds of the formulae (I) and (IV), and compounds of (II) and (IV) is similarly feasible.

When the compound of formula (I), the compound of formula (III) and acetone are mixed in a mole ratio of 1:1:1 and interacted, the reaction proceeds according to the following reaction formula (3)

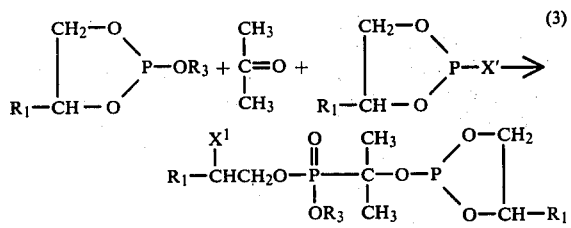

(3)

In the reaction, the compounds of formula (I) and (III) may be prepared separately, and then react with acetone. Alternatively, the compound of formula (I) is reacted with a half equivalent of an oxide or an alcohol to produce the compound of formula (III), thereby giving a mixture of the compounds of formulae (I) and (III) in a mole ratio 1:1. The mixture is then added with acetone to undergo the reaction mentioned above. In a strict sense, it is preferred that the mole ratio of the compound of formula (I), the compound of formula (III) and acetone is 1:1:1. However, many difficulties are encountered in severely controlling the mole ratios at 1:1:1. In practice, the mole ratios will suffice to be at approximately 1:1:1. Especially when contamination of small amounts of a phosphorus monomer and a compound of the formula (VII) in which n is an integer from 1 to 3 is allowable, these mole ratios are not necessarily severely controlled. It has been confirmed that the compound of the invention does not lose its characteristic features by such contamination. It has been confirmed that the reaction product obtained by the reaction (3) does not undergo polymerization when allowed to stand for 1 day to 1 week after completion of the reaction with acetone.

The product of the formula (3) is ring opened at the cyclic phosphite moiety by means of molecular halogen $(X^2)_2$ according to the following reaction formula (4)

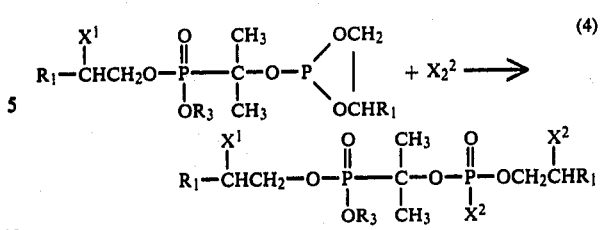

(4)

The halogen atom attached to the phosphorus atom of the resulting product is relatively active. Thus, the product is subsequently reacted with an oxide or an alcohol for esterification according to the following reaction formula (5) to obtain the final organic phosphorus compound:

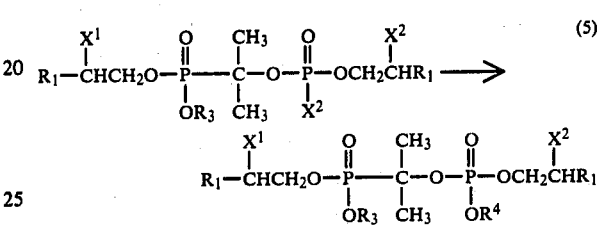

(5)

The preferred embodiment of the production process will be described in detail.

The compound of formula (I) or (II) which is used as one of the starting materials can be obtained by the reaction shown in the formula (1). This reaction is feasible either by dropwise adding a phosphorus trihalide and a glycol in a mole ratio of 1:1 to a reactor containing solvent, or by dropping a glycol into an excess phosphorus trihalide and then removing an excess of the phosphorus trihalide by distillation. It is important to note that presence of an excess of glycol in the reaction system must be avoided. The resulting cyclic halogenophosphite is esterified with an oxide or an alochol to produce a cyclic phosphorous acid ester expressed by the formula (III) or (IV). The esterification reaction is conducted at a temperature ranging from −50° to 100° C., preferably 0° to 20° C. Examples of the oxides are alkylene oxides or halogenated alkylene oxides such as ethylene oxide, propylene oxide, epichlorohydrin, epibromohydrin, etc. Examples of alcohols are alkyl alcohols or halogenated alkyl alcohols such as methyl alcohol, ethyl alcohol, n-butyl alcohol, isobutyl alcohol, ethylene chlorohydrin, ethylene bromohydrin, propylene chlorohydrin, 2,3-dichloropropanol, 2,3-dibromopropanol, and the like. The esterification reaction is feasible by any known techniques.

The reaction with acetone may be conducted either by dropping an equimolar quantity of acetone into a mixture of the compound of formula (I) or (II) and the compound of formula (III) or (IV) in a mole ratio of 1:1, or by dropping an equimolar quantity of the compound of formula (I) or (II) into a mixture of the compound of formula (III) or (IV) and acetone in mole ratio of 1:1. Alternatively, a half molar equivalent of the compound of formula (I) or (II) is first esterified to give a mixture of the compounds of formulae (I) and (III) or the compounds of formulae (II) and (IV) in equimolar quantities. Then, acetone is dropped into such mixture for reaction. This reaction is generally conducted at a temperature ranging from −50° C. to 100° C., preferably 0° to 50° C.

Then, the resulting product is reacted with a halogen at a temperature of −50° to 100° C., preferably 0° to 50° C. Bromine or chlorine is especially useful for this purpose. The completion of the halogenation reaction is confirmed by the fact that the heat of reaction stops generating or that the decoloration by halogen is stopped. It is important that, after completion of the reaction, the halogen remaining in the reaction system is completely purged by introduction with an inert gas such as, for example, nitrogen gas. The remaining halogen will adversely affect the subsequent esterification reaction.

The halogenated product thus obtained is then reacted with the same type of oxides or alcohols as used hereinbefore, to give a final compound.

For this esterification reaction, catalysts are generally used with attendant advantages that the reaction time is shortened, that the reaction is feasible at lower temperatures, and that the reaction yield is enhanced. The catalysts useful for this purpose include, for example, titanium tetrachloride, aluminum chloride, zirconium tetrachloride, ferric chloride, boron trifluoride, tin tetrachloride, iron powder made by cutting, ammonium meta-vanadate, phosphorus trichloride, phosphorus tribromide, pyridine, tri-n-butylamine, quinoline, aniline, N,N-dimethylaniline, tetrabutyl titanate, hydrochloric acid, sulfuric acid, boric acid and the like.

In general, the reaction of formula (5) is effected at a moderately high temperature ranging from 0° to 160° C., preferably 30° to 90° C., which may vary depending on the groups being reacted, the kind of the reactants and the kind of the catalyst.

In the production of the organic phosphorus compound as described hereinabove, the reaction are feasible in the absence of solvent. However, use of solvent is very effective in controlling the reaction system, improving the yield, and suppressing side reactions. The solvents useful for the process of the invention are inactive organic liquids. Most preferable examples of such solvents include benzene, toluene, 1,1,2-trichloroethane, chloroform, carbon tetrachloride, ethylene dichloride, chlorobenzene, cyclohexane, and n-hexane. The amount of the solvent employed for the reaction is in the range of 0–100 parts by volume, preferably 1–10 parts by volume, per part by volume of the cyclic halogenophosphite. The solvent for the reaction can be completely recovered.

The reaction product obtained according to the reaction formula (5) may contain the solvent used for the reaction and small amounts of substances of low boiling point. However, these solvent substances can be readily removed by distillation. If the final product of formula (5) contains small amount of acidic substance or if it is needed to remove the catalyst for the esterification, the product is washed with an aqueous alkali solution, followed by removing the water under reduced pressure and drying to obtain a final product.

The thus obtained organic phosphorus compound is found to be excellent particularly as an addition-type flame retardant for polyurethane foam as well as for synthetic fibers, natural fibers, polyvinyl chloride, polystyrene, polyester, polyethylene, etc. This compound may be also useful as a plasticizer for plastics and an additive for gasoline.

The present invention will be particularly illustrated by way of the following Synthetic Example and Examples.

EXAMPLE OF SYNTHESIS OF CYCLIC HALOGENOPHOSPHITE (1) 161.2 g (1.15 moles) of phosphorus trichloride (purity 98%) was introduced into a flask, to which 65.3 g (1 mole) of ethylene glycol (purity 95%) was added dropwise with agitation at 15°–20° C. in 1 hour. The produced hydrogen chloride was discharged from the reaction system and absorbed in an aqueous alkali solution. Upon the discharge, part of the phosphorus trichloride was also discharged by entrainment in the discharged hydrogen chloride. After completion of the addition, the reaction system was further agitated at 15°–20° C. for 30 minutes and then an excess of phosphorus trichloride was removed under a reduced pressure (15 mmHg/30° C.) to obtain 2-chloro-1,3,2-dioxaphosphoran at a yield of 100%.

(2) 300 ml of benzene used as solvent was introduced into a flask and nitrogen gas was blown into the benzene. The benzene was heated to 30°–35° C. under agitation, into which 140.2 g of phosphorus trichloride (purity 98%) and 65.3 g (1 mole) of ethylene glycol (purity 95%) were simultaneously dropped in 1 hour while maintaining a $PCl_3/HOCH_2CH_2OH$ mole ratio of 1.0. The produced hydrogen chloride was discharged outside the reaction system by means of the nitrogen stream and absorbed in an aqueous alkali solution. After completion of the dropping, the charge of the nitrogen gas was continued for 30 minutes at 30°–50° C. while agitating. As a result, 2-chloro-1,3,2-dioxaphosphoran was obtained at a yield of 100%.

The cyclic halogenophosphite prepared by the above procedure may be used as starting material in the form of the benzene solution, or may be used after removal of benzene under a reduced pressure (50–80 mmHg/35°–40° C.).

EXAMPLE 1

Into 126.5 g (1 mole) of 2-chloro-1,3,2-dioxaphosphoran,

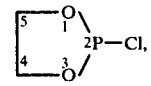

prepared according to the procedure (1) of the Synthetic Example was dropped 29 g (0.5 moles) of propylene oxide at a temperature below 20° C. in 1 hour, followed by agitating for 30 minutes. Then, 29 g (0.5 moles) of acetone was dropwise added to the mixture at a temperature of 25° to 40° C. in 1 hour, followed by agitating for further 30 minutes. Chlorine was blown into the mixture at a temperature of 5° to 20° C. for reaction. When the reaction solution was colored in yellow, the charge of chlorine was stopped. An excess of chlorine was removed by means of a stream of nitrogen gas to obtain 220 g of a colorless, transparent, viscous liquid. To the liquid thus obtained were added first 0.4 g of titanium tetrachloride at room temperature and then 29 g (0.5 moles) of propylene oxide at a temperature of 30° C. over 1 hour. Thereafter, the mixture was heated up to 70° C., to which was dropwise added 5.8 g (0.1 mole) of propylene oxide over 30 minutes. Thereafter, the reaction solution was heated to 80° C. and agitated for 1 hour to complete the reaction. After the completion of the reaction, the solution was washed with 200 ml of an aqueous 5% sodium carbonate solution and then with each 200 ml of water two times. After washing, the solution was treated at a bath temperature of 60° C. under a reduced pressure of 3 to 4 mmHg for 1 hour to remove substances of low boiling point consisting principally of water to obtain 232 g (at a yield of 93%) of a colorless, transparent, relatively viscous liquid of substance having the following structural formula

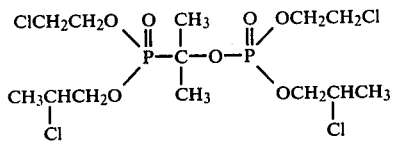

Elementary Analysis: Calculated for $C_{13}H_{26}Cl_4O_7P_2$ (%): C: 31.35; H: 5.25; Cl: 28.47; P: 12.44; Found (%): C: 30.88; H: 5.54; Cl: 28.30; P: 12.77.

EXAMPLE 2

29 g (0.5 moles) of propylene oxide was dropwise added at a temperature of 0° to 5° C. in 1 hour to 198 g of a solution, in benzene, of 0.5 moles of 2-chloro-4-methyl-1,3,2-dioxa phosphorinan,

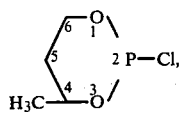

synthesized according to the procedure (2) of Synthetic Example using phosphorus trichloride and 1,3-butandiol as starting materials. The mixture was agitated for 30 minutes. To the mixture was further added 198 g of a solution, in benzene, of 0.5 moles of 2-chloro-4-methyl-1,3,2-dioxaphosphorinan. To the resulting mixture was added 29 g (0.5 moles) of acetone in 1 hour while cooling the mixture down to 10°-20° C., followed by agitating for further 30 minutes. Thereafter, chlorine was passed into the reaction solution while maintaining the reaction solution at temperatures below 40° C. When the reaction solution was colored in yellow, the charge of chlorine was stopped. An excess of chlorine present in the solution was removed by means of a stream of nitrogen gas to obtain 490 g of a colorless, transparent benzene solution. To the solution was added 0.6 g of titanium tetrachloride at room temperature. The solution was heated to and maintained at 40° C., to which was further added dropwise 29 g (0.5 moles) of propylene oxide in 1 hour. The reaction solution was heated to 60° C., into which 5.8 g (0.1 mole) of propylene oxide was further added in 30 minutes. After completion of the dropping, the solution was agitated for 1 hour. The resulting colorless, transparent solution was washed first with 300 ml of an aqueous 10% sodium carbonate solution and then with each 300 ml of saturated brine two times. After washing, the benzene was removed by distillation from the solution, followed by separating substances of low boiling point principally composed of water under a reduced pressure of 3-4 mmHg to obtain 249 g (at a yield of 90%) a colorless, transparent, viscous liquid of substance having the following structural formula

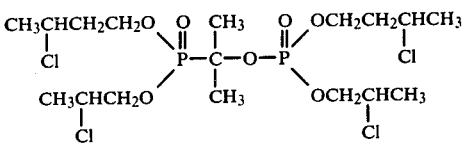

Elementary Analysis: Calculated for $C_{17}H_{34}Cl_4O_7P_2$ (%): C: 36.84; H: 6.18; Cl: 25.59; P: 11.18; Found (%): C: 36.35; H: 5.98; Cl: 25.79; P: 11.50

EXAMPLE 3

140.5 g (1 mole) of 2-chloro-4-methyl-1,3,2-dioxaphosphoran synthesized according to the procedure (1) of the Synthetic Example using phosphorus trichloride and propylene glycol as starting materials was dissolved in 200 ml of carbon tetrachloride. 39.6 g (0.5 moles) of pyridine was added to the solution at room temperature, into which 16 g (0.5 moles) of methanol was dropped over 30 minutes while violently agitating. After completion of the dropping, the reaction was continued for 2 hours. After completion of the reaction, colorless crystals of the pyridine-hydrochloric acid salt was separated by filtration and washed with 50 ml of carbon tetrachloride. The filtrate and the washing were combined together. Into the mixture was dropped 29 g (0.5 moles) of acetone in 1 hour at a temperature of 30° to 40° C., followed by agitating for 30 minutes. Similarly to the case of Example 1, chlorine was then charged for reaction, after which 39.6 g (0.5 moles) of pyridine was added to the reaction solution. Thereafter, 16 g (0.5 moles) of methanol was dropwise added to the solution at room temperature in 30 minutes while violently agitating. After completion of the dropping, the reaction was continued for 2 hours. After completion of the reaction, colorless crystals of the pyridine-hydrochloric acid salt were removed by filtration and washed with 50 ml of carbon tetrachloride. The filtrate and the washing were combined together and then the mixture was washed successively with: (a) 200 ml of an aqueous 15% sodium carbonate solution, (b) 200 ml of water, and (c) another 200 ml of water. The thus washed solution was subjected to distillation to remove the carbon tetrachloride. The thus removed liquid was placed in a bath of 50° C. to remove substances of low boiling point under a reduced pressure of 3-4 mmHg thereby obtaining 182.5 g (at a yield of 91%) of a relatively viscous, transparent liquid of substance having the following structural formula

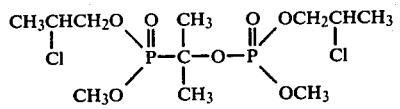

Elementary Analysis: Calculated for $C_{11}H_{24}O_7Cl_2P_2$ (%): C: 32.92; H: 5.99; Cl: 17.71; P: 15.46; Found (%): C: 33.20; H: 6.10; Cl: 17.50; P: 15.19

EXAMPLE 4

200 ml of benzene was added to 63.3 g (0.5 moles) of 2-chloro-1,3,2-dioxaphosphoran synthesized according to the procedure (1) of the Synthetic Example, followed by agitating to give a uniform solution. 50.5 g (0.5 moles) of triethylamine was added to the solution at room temperature, into which 37 g (0.5 moles) of n-butyl alcohol was dropped in 1 hour. After the dropping, the solution was agitated at room temperature for 2 hours. The resulting precipitate of triethylamine hydrochloride was separated by filtration and then washed with 30 ml of benzene. The filtrate and the washing were combined together, to which was added 63.3 g (0.5 moles) of 2-chloro-1,3,2-dioxaphosphoran. Thereafter, 29 g (0.5 moles) of acetone was gradually dropped into the mixture so that the reaction temperature did no exceed 40° C. The dropping was completed in 1 hour, after which the mixture was agitated for 30 minutes. The reaction solution was maintained at 35° C.–40° C., into which chlorine was passed to undergo a halogenation reaction until the solution was colored in yellow. An excess of chlorine was removed by means of a stream of nitrogen gas to obtain a colorless benzene solution. 50.5 g (0.5 moles) of triethylamine was added to the solution at room temperature, into which was gradually added 37 g (0.5 moles) of n-butyl alcohol over 1 hour. After the dropping, the mixture was agitated for 2 hours and the resulting precipitate of triethylamine hydrochloride was removed by filtration. The precipitate was washed with 50 ml of benzene. The filtrate and the washing were combined together, which was washed with 200 ml of an aqueous 15% sodium carbonate solution and then with each 200 ml of water two times. After separation of the organic layer, benzene was removed by distillation from the solution, from which were also removed by distillation substances of low boiling point principally composed of water by heating the solution at 60° C. under a reduced pressure (of 3–5 mmHg). As a result, there was obtained 203 g (at a yield of 89%) of a colorless, viscous liquid of substance expressed by the following structural formula

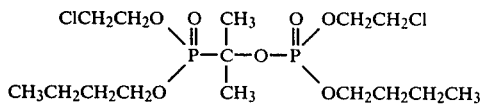

Elementary Analysis: Calculated for $C_{15}H_{32}Cl_2O_7P_2$ (%): C: 39.40; H: 7.05; Cl: 15.51; P: 13.55; Found (%): C: 39.10; H: 7.00; Cl: 15.80; P: 13.45

EXAMPLE 5

68.5 g (0.5 moles) of epibromohydrin was dropped at a temperature below 20° C. in 1 hour into 126.5 g (1 mole) of 2-chloro-1,3,2-dioxaphosphoran synthesized by the procedure (1) of the Synthetic Example. Then, the solution was agitated for 30 minutes for reaction. The resulting reaction solution was heated to and maintained at 25°–40° C., into which was gradually dropped 29 g (0.5 moles) of acetone. The dropping was completed in 1 hour and agitation was continued for further 30 minutes. Then, the reaction solution was treated with chlorine similarly to the case of Example 1. The thus treated solution was then added with 0.6 g of titanium tetrachloride at room temperature and was heated to 70° C., into which was dropped 82.1 g (0.6 moles) of epibromohydrin over 1 hour. The mixture was heated to 80° C. and further agitated for 30 minutes to complete the reaction. The resulting reaction solution was washed with 200 ml of an aqueous 5% sodium carbonate solution and then with each 200 ml of water two times. The thus washed solution was placed in a bath of 60° C. to remove substances of low boiling point principally composed of water by distillation under a reduced pressure (of 3–5 mmHg) thereby obtaining 295 g (at a yield of 90%) of a pale yellow viscous liquid of substance expressed by the following structural formula

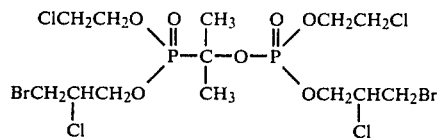

Elementary Analysis: Calculated for $C_{13}H_{24}Br_2Cl_4O_7P_2$ (%): C: 23.81; H: 3.69; Br: 24.37; Cl: 21.62; P: 9.45; Found (%): C: 24.01; H: 3.51; Br: 24.19; Cl: 21.70; P: 9.32

EXAMPLE 6

126.5 g (1 mole) of 2-chloro-1,3,2-dioxaphosphoran which had been synthesized according to the procedure (2) of the foregoing Synthetic Example and from which the benzene used as solvent had been removed was treated in the same manner as in Example 1 to obtain a product reacted with acetone. Then, 96 g (0.6 moles) of bromine was vaporized and charged into the reaction solution at room temperature. After completion of the halogenation reaction, unreacted bromine was removed by passing a nitrogen stream into the reaction system to obtain 265 g of a pale yellow, transparent, viscous liquid. To the thus obtained reaction product were added 0.6 g of titanium tetrachloride at room temperature and then 35 g (0.6 moles) of propylene oxide at 40° C. The mixture was heated to 70° C. and agitated for 1 hour to complete the reaction. The reaction solution was admixed with 200 ml of benzene, followed by washing with 200 ml of an aqueous 5% sodium carbonate solution and then with each 200 ml of water two times. The thus washed solution was heated at 60° C. under a reduced pressure (3–5 mmHg) to remove substances of low boiling point principally composed of water by distillation. As a result, 264 g (at a yield of 90%) of a pale yellow viscous liquid of substance having the following structural formula was obtained.

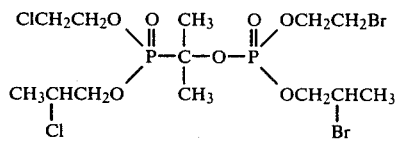

Elementary Analysis: Calculated for $C_{13}H_{26}Br_2Cl_2O_7P_2$ (%): C: 26.60; H: 4.47; Br: 27.22; Cl: 12.03; P: 10.55; Found (%): C: 26.48; H: 4.72; Br: 27.10; Cl: 12.11; P: 10.49

EXAMPLE 7

22 g (0.5 moles) of ethylene oxide was introduced at a temperature below 20° C. in 1 hour into 85.5 g (0.5 moles) of 2-bromo-1,3,2-dioxaphosphoran which had been prepared according to the procedure (1) of the foregoing Synthetic Example using phosphorus tribromide and ethylene glycol as starting materials. To the mixture was added 85.5 g (0.5 moles) of 2-bromo-1,3,2-dioxaphosphoran synthesized similarly to the above procedure. Then, 29 g (0.5 moles) of acetone was dropped into the mixture at a temperature below 40° C. in in 1 hour. The mixture was agitated for 30 minutes and then introduced with bromine in the same manner as in Example 6. After the introduction, unreacted bromine was removed by passage of nitrogen into the reaction system to obtain 302 g of a pale yellow, transparent, viscous liquid. To the thus obtained reaction product were added 0.7 g of titanium tetrachloride at room temperature and then 26 g (0.6 moles) of ethylene oxide at 25°–30° C. The mixture was heated up to 60° C. and agitated for 1 hour to complete the reaction. The resulting reaction product was washed with 200 ml of an aqueous 5% sodium carbonate and then with each 200 ml of water two times. The thus washed product was heated at 60° C. for distillation under a reduced pressure (3–5 mmHg) to remove the contaminants of low boiling point substantially composed of water thereby obtaining 295 g (at a yield of 91%) of a pale yellow viscous liquid of substance having the following structural formula

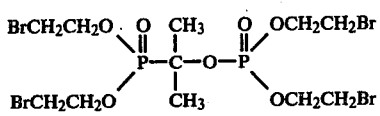

Elementary Analysis: Calculated for $C_{11}H_{22}Br_4O_7P_2$ (%); C: 20.39; H: 3.42; Br: 49.33; P: 9.56; Found (%): C: 20.60; H: 3.50; Br: 49.12; P: 9.45

EXAMPLE 8

29 g (0.5 mole) of propylene oxide was introduced at a temperature below 20° C. in 1 hour into 63.3 g (0.5 mole) of 2-chloro-1,3,2-dioxaphosphoran which had been synthesized according to the procedure (1) of the foregoing Synthetic Example. Then, the solution was agitated for 30 minutes for reaction. To the mixture was added 70.3 g (0.5 mole) of 2-chloro-1,3,2-dioxyphosphorinan which had been synthesized according to the procedure (1) of the foregoing Synthetic Example using phosphorus trichloride and 1,3-propandiol as starting material. The resulting reaction solution was heated to and maintained at 20°–40° C., into which was gradually dropped 29 g (0.5 mole) of acetone. The dropping was completed in 1 hour and agitation was continued for further 30 minutes.

Chlorine was blown into the mixture at a temperature of 5° to 20° C. for reaction. When the reaction solution was colored in yellow, the charge of chlorine was stopped. An excess of chlorine was removed by means of a stream of nitrogen gas to obtain 227 g of colorless, transparent, viscous liquid.

To the liquid thus obtained were added first 0.4 g of titanium tetrachloride at room temperature and then 26 g (0.5 mole) of ethylene oxide at a temperature below 50° C. over 1 hour.

Thereafter, the reaction solution was heated 70°–80° C. and agitated for 1 hour to complete the reaction.

After the completion of the reaction, the solution was washed with 200 ml of an aqueous 5% sodium carbonate solution and then with each 200 ml of water two times. After washing, the solution was treated at a bath temperature of 60° C. under a reduced pressure of 3 to 4 mmHg for 1 hour to remove substance of low boiling point consisting principally of water to obtain 235 g (at a yield of 95%) of a colorless, transparent, relatively viscous liquid of substance having the following stractual formula

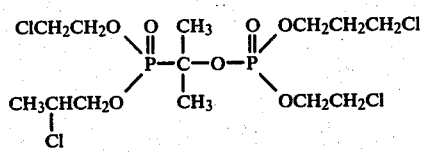

Elementary Analysis: Calculated for $C_{13}H_{26}Cl_4O_7P_2$ (%): C: 31.35; H: 5.25; Cl: 28.47; P: 12.44; Found (%): C: 30.95; H: 5.35; Cl: 28.10; P: 12.56

EXAMPLE 9

29 g (0.5 mole) of propylene oxide was introduced at a temperature below 20° C. in 1 hour into 70.3 g (0.5 mole) of 2-chloro-1,3,2-dioxaphosphorinan which had been prepared according to the procedure (1) of the foregoing Synthetic Example using phosphorus trichloride and ethyleneglycol as starting materials. Then, the solution was agitated for 30 minutes for reaction. The resalting reaction solution was heated to and maintained at 25°–40° C. into which was gradually dropped 29 g (0.5 mole) of acetone.

Then, 63.3 g (0.5 mole) of 2-chloro-1,3,2-dioxaphosphoran which had been prepared according to the procedure (1) of the foregoing Synthetic Example, was dropped into the mixture at a temperature of 20°–40° C. in 1 hour, followed by agitating for further 30 minutes.

Chlorine was blown into the mixture at a temperature of 5° C. to 20° C. for reaction.

When the reaction solution was colored in yellow, the charge of chlorine was stopped. An excess of chlorine was removed by means of stream of nitrogen gas to obtain 227 g of a colorless, transparent, viscous liquid.

To liquid thus obtained were added first 0.4 g of titanium tetrachloride at a room temperature and the 29 g (0.5 mole) of propylene oxide at a temperature below 50° C. over 1 hour.

Thereafter, the mixture was heated up to 70°–80° C. and agitated for 1 hour to complete the reaction. After the completion of the reaction, the solution was washed with 200 ml of an aqueous 5% sodium carbonate solution and then with each 200 ml of water two times.

After washing, the solution was treated at a bath temperature of 60° C. under a reduced pressure of 3 to 4 mmHg for 1 hour to remove substance of low boiling point principally composing of water to obtain 238 g (at a yield of 93%) of colorless, transparent relatively viscous liquid of substance having the following stractual formula

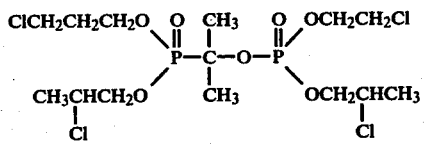

Elementary Analysis: Calculated for $C_{14}H_{28}Cl_4O_7P_2$ (%): C: 32.83; H: 5.81; Cl: 27.69; P: 12.10; Found (%): C: 32.71; H: 5.61; Cl: 27.80; P: 12.05

What is claimed is:

1. A process for preparing an organic phosphorus compound of the following general formula

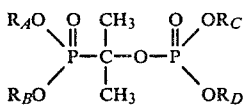

wherein $R_A$ represents $R_1-CH-Y-$
$\quad\quad\quad\quad\quad\quad\quad\quad\quad\quad\quad |$
$\quad\quad\quad\quad\quad\quad\quad\quad\quad\quad\quad X^1$ where $X^1$ is a halogen atom,
Y is $-CH_2-$ or $-CH_2-CH_2-$, and
$R_1$ is H or $CH_3$ when Y is $-CH_2-CH_2-$, or H, $CH_3$ or $C_2H_5$ when Y is $-CH_2-$,
$R_B$ represents an alkyl group having from 1 to 4 carbon atoms or a halogenated alkyl group having from 2 to 4 carbon atoms,
$R_C$ represents

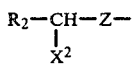

where $X^2$ is a halogen atom,
Z is $-CH_2-$ or $-CH_2-CH_2-$, and
$R_2$ is H or $CH_3$ when Z is $-CH_2-CH_2-$, or H, $CH_3$ or $C_2H_5$ when Z is $-CH_2-$, and
$R_D$ represents an alkyl group having from 1 to 4 carbon atoms or a halogenated alkyl group having from 2 to 4 carbon atoms, said process comprising the steps of:
reacting (a) a cyclic halogenophosphite of the general formula

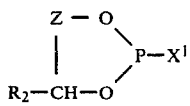

wherein $X^1$, Z and $R_2$ have the same meanings as given above, with (b) a cyclic phosphorous acid ester of the general formula

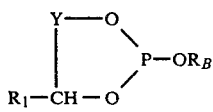

wherein $R_1$, Y and $R_B$ have the same meanings as given above, and (c) acetone with a mole ratio of halogenophosphite: phosphorous acid ester: acetone of about 1:1:1, the resulting product being reacted with a molecular halogen $X_2^2$ to give a first product of the general formula

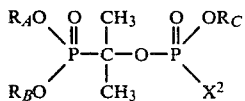

wherein $R_A$, $R_B$, $R_C$ and $X_2$ have the same meanings as given above; and
reacting said first product with an alkyl or halogenated alkyl alcohol or an alkylene oxide or halogenated alkylene oxide, thereby esterifying said first product to give said organic phosphorus compound.

2. The process as claimed in claim 1, wherein said halogenophosphite is 2-chloro-1,3,2-dioxaphosphoran, said phosphorous acid ester is 2-(2-chloropropoxy)-1,3,2-dioxaphosphoran, said molecular halogen is chlorine and said alkylene oxide is propylene oxide, thereby to obtain an organic phosphorus compound of the formula

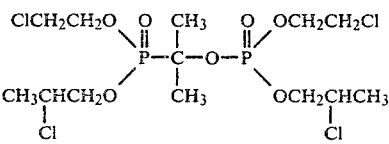

3. The process as claimed in claim 1, wherein said halogenophosphite is 2-chloro-4-methyl-1,3,2-dioxaphosphorinan, said phosphorous acid ester is 2-(2-chloropropoxy)-4-methyl-1,3,2-dioxaphosphorinan, said molecular halogen is chlorine and said alkylene oxide is propylene oxide, thereby to obtain an organic phosphorus compound of the formula

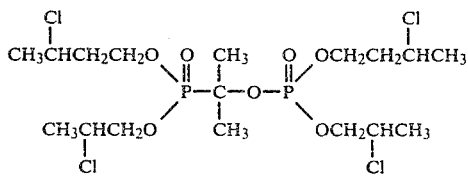

4. The process as claimed in claim 1, wherein said halogenophosphite is 2-chloro-4-methyl-1,3,2-dioxaphosphoran, said phosphorous acid ester is 2-methoxy-4-methyl-1,3,2-dioxaphosphoran, said molecular halogen is chlorine and said alkyl alcohol is methanol, thereby to obtain an organic phosphorus compound of the formula

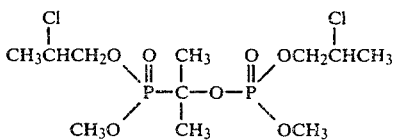

5. The process as claimed in claim 1, wherein said halogenophosphite is 2-chloro-1,3,2-dioxaphosphoran, said phosphorous acid ester is 2-n-butoxy-1,3,2-dioxaphosphoran, said molecular halogen is chlorine and said alkyl alcohol is n-butyl alcohol, thereby to obtain an organic phosphorus compound of the formula

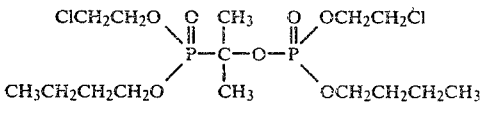

6. The process as claimed in claim 1, wherein said halogenophosphite is 2-chloro-1,3,2-dioxaphosphoran, said phosphorous acid ester is 2-(3-bromo-2-chloropropoxy)-1,3,2-dioxaphosphoran, said molecular halogen is chlorine and said halogenated alkylene oxide is epibromohydrine, thereby to obtain an organic phosphorus compound of the formula

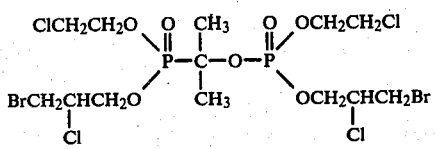

7. The process as claimed in claim 1, wherein said halogenophosphite is 2-chloro-1,3,2-dioxaphosphoran, said phosphorous acid ester is 2-(2-chloropropoxy)-1,3,2-dioxaphosphoran, said molecular halogen is bromine and said alkylene oxide is propylene oxide, thereby to obtain an organic phosphorus compound of the formula

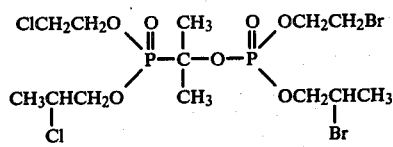

8. The process as claimed in claim 1, wherein said halogenophosphite is 2-bromo-1,3,2-dioxaphosphoran, said phosphorous acid ester is 2-(2-bromoethoxy)-1,3,2-dioxaphosphoran, said molecular halogen is bromine and said alkylene oxide is ethylene oxide, thereby to obtain an organic phosphorus compound of the formula

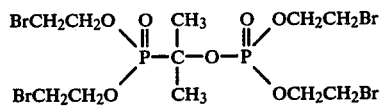

9. The process as claimed in claim 1, wherein said halogenophosphite is 2-chloro-1,3,2-dioxaphosphorinan said phosphorous acid ester is 2-(2-chloropropoxy)-1,3,2-dioxaphosphoran, said molecular halogen is chlorine and said alkylene oxide is ethylene oxide, thereby to obtain an organic phosphorus compound of the formula

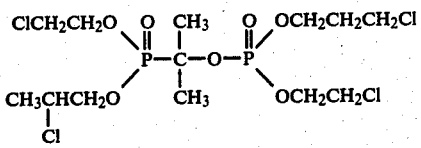

10. The process as claimed in claim 1, wherein said halogenophosphite is 2-chloro-1,3,2-dioxaphosphoran, said phosphorus acid ester is 2-(2-chloropropoxy)-1,3,2-dioxaphosphorinan, said molecular halogen is chlorine and said alkylene oxide is propylene oxide, thereby to obtain an organic phosphorus compound of the formula

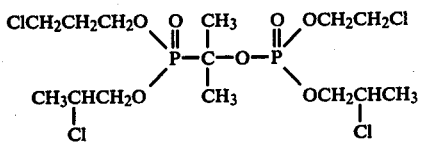

11. The process as claimed in claim 1, wherein said reaction of said halogenophosphite with said phosphorus acid ester and acetone is carried out in an organic solvent.

12. The process as claimed in claim 11, wherein said organic solvent is selected from the group consisting of benzene, toluene, 1,1,2-trichloroethane, chloroform, carbon tetrachloride, ethylene dichloride, chlorobenzene, cyclohexane and n-hexane.

13. The process as claimed in claim 1, wherein both said reaction of said halogenophosphite with said phosphorous acid ester and said acetone and said halogenation reaction are performed at a temperature between −50° and 100° C.

14. The process as claimed in claim 1, wherein said molecular halogen is chlorine or bromine.

15. The process as claimed in claim 1, wherein said reaction of said first product with said alcohol or said oxide is performed in the presence of a catalyst.

16. The process as claimed in claim 15, wherein said catalyst is selected from the group consisting of titanium tetrachloride, pyridine, triethylamine.

17. The process as claimed in claim 1, wherein said reaction of said first product with said alcohol or said oxide is performed at a temperature between 0° and 160° C.

* * * * *

UNITED STATES PATENT OFFICE
CERTIFICATE OF CORRECTION

Patent No. 4,196,155　　　　　　Dated April 1, 1980

Inventor(s) Isamu Yamamoto; Eiichi Noda; and Yoshiaki Noguchi

It is certified that error appears in the above-identified patent and that said Letters Patent are hereby corrected as shown below:

In the Abstract, third line, please change

" 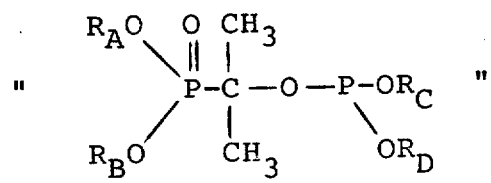 "

-- 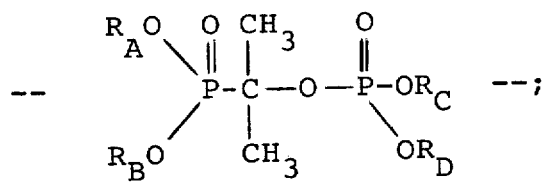 --;

In the Abstract, 21st line, please change

"$R_d$" to --$R_D$--.

Signed and Sealed this

Twenty-second Day of July 1980

[SEAL]

Attest:

SIDNEY A. DIAMOND

Attesting Officer　　　Commissioner of Patents and Trademarks